United States Patent [19]

Witherspoon et al.

[11] Patent Number: 4,625,570
[45] Date of Patent: Dec. 2, 1986

[54] STOCK SAMPLING DEVICE

[75] Inventors: Kent Witherspoon; James P. Carroll; Bud Allen, all of Decatur; Terri Norton; James Odell, both of Town Creek; Doreen Pittman, Florence; Pat Phillips, Hillsboro; Phillip Everett, Muscle Shoals; Joe Hovater, Decatur; Hank Livingston, Decatur; Lisa Williams-Terry, Decatur, all of Ala.

[73] Assignee: Champion International Corporation, Stamford, Conn.

[21] Appl. No.: 789,148

[22] Filed: Oct. 18, 1985

[51] Int. Cl.[4] ............................................. G01N 1/20
[52] U.S. Cl. ................................................. 73/863.81
[58] Field of Search ........... 73/863.81, 863.82, 863.83, 73/863.84, 863.85, 863.86, 864, 864.51; 162/49, 263, 198

[56] References Cited

U.S. PATENT DOCUMENTS

| 1,966,712 | 7/1934 | Fisher et al. | 73/21 |
|---|---|---|---|
| 2,370,260 | 2/1945 | Robison | 73/422 |
| 2,683,373 | 7/1954 | Gallup et al. | 73/422 |
| 3,034,360 | 5/1962 | Hampl | 73/425 |
| 3,066,539 | 12/1962 | Coker et al. | 73/423 |
| 3,747,411 | 7/1973 | McDermott et al. | 73/423 R |
| 3,949,614 | 4/1976 | Abonnenc | 73/863.83 |
| 4,294,124 | 10/1981 | Kalwaitis | 73/863.85 |

Primary Examiner—Stewart J. Levy
Assistant Examiner—Robert R. Raevis
Attorney, Agent, or Firm—Evelyn M. Sommer; William W. Jones

[57] ABSTRACT

A device for removing samples of a material which is dropped through a vertical pipeline. The device includes a scoop which can be telescoped into the pipeline through a side mounting track to catch a material sample, and then telescoped out of the pipeline into the mounting track. The mounting track has a lower discharge opening which registers with the scoop when the latter is rotated 180° so that the sample can be dropped into a container. The inner end of the scoop is closed so that the pipeline remains closed during all phases of the sampling operation. The mounting track is secured to a nozzle on the pipeline.

2 Claims, 5 Drawing Figures

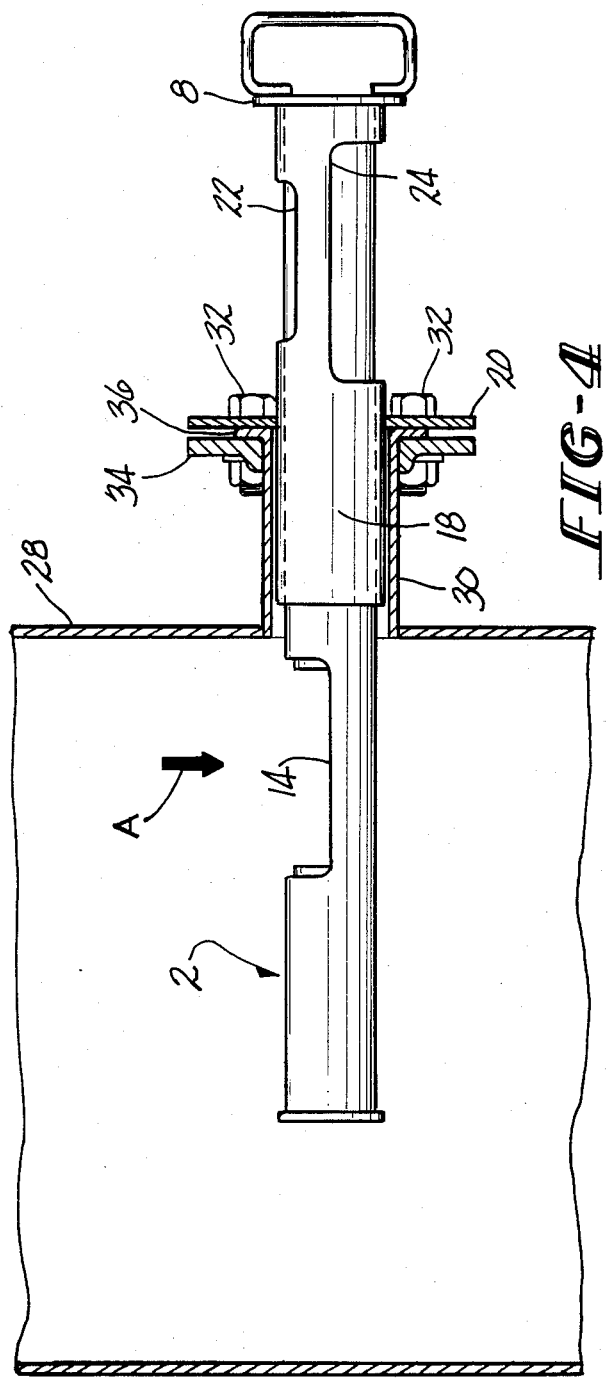
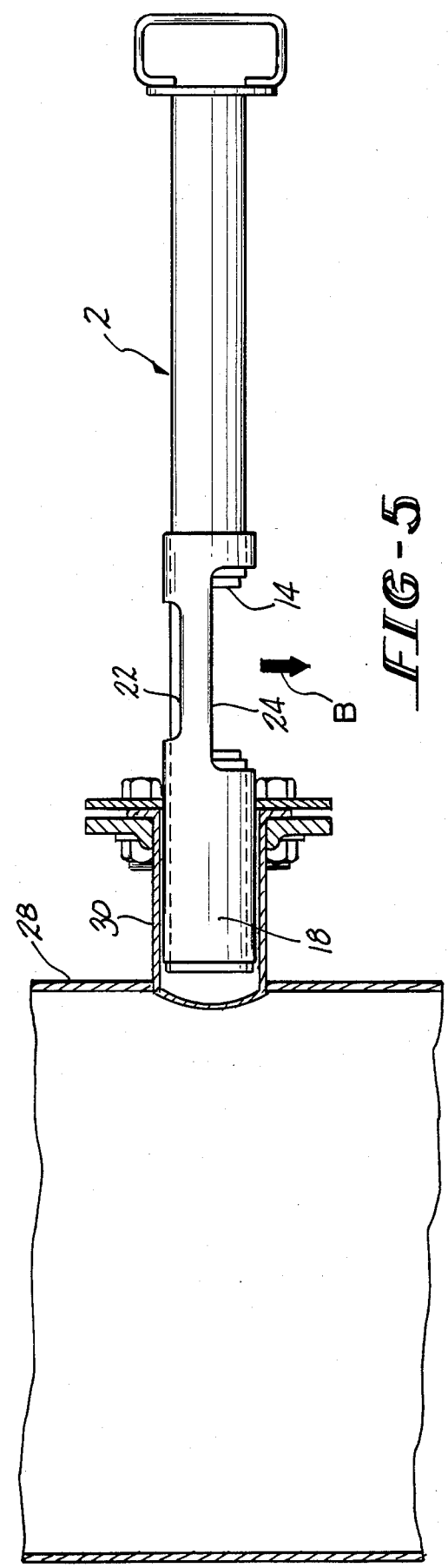

STOCK SAMPLING DEVICE

This invention relates to a device for securing material samples from a material feed or processing pipeline through which the material falls vertically.

In various material processing lines, it may be desirable to take samples of the material being processed at one or more intermediate stages of the process. Such is the case with pulp bleaching towers in paper mills. In a pulp bleaching tower, the pulp is pumped into the bottom of each tower with a thick stock pump. The pulp thus flows upwards within the tower until it is scraped off the top by a rotating paddle/scraper device. The scraped pulp is then fed by the scraper into a chute or downleg where it gravity-falls into the thick stock pump for the next tower.

The downleg is typically a twenty-inch diameter stainless steel pipe which has a flanged nozzle welded to its exterior near its top. A gate valve is bolted to the nozzle so that when a sample is to be taken, the valve is opened and a stainless steel pipe scoop is inserted into the downleg via the nozzle to catch some of the free falling pulp. When the scoop is withdrawn from the nozzle, the gate valve is closed, the sample removed, and the scoop set aside. With this type of prior art sampler, the nozzle fills up inside with the pulp between samplings, thus creating the possibility of contamination of the subsequent sample catch. Also, the need to simultaneously operate the valve, scoop and sample container is difficult and awkward.

The sampler of this invention includes a scoop which remains in place in a carrier track which is bolted onto the sampler nozzle. The gate valve is removed, and the inner end of the scoop serves as a valve for preventing the pulp or other material from entering the nozzle between samplings. The scoop is telescoped into the carrier track to be reciprocable into and out of the pipeline. The track has an opening in its underside which can register with the open top of the scoop when the latter is rotated through a 180° angle in the carrier after the scoop is withdrawn from the pipeline. The sample is taken by pushing the scoop into the pipeline right-side-up so that the material falling through the pipeline will fall into the scoop. The scoop is then pulled out of the pipeline an rotated about its axis 180° to align its open top with the opening in the underside of the track. The sample is thus dumped into a test container and the scoop is then rotated back to its upright position. The scoop will then remain in the track with its inner end protecting the nozzle against entry of the material falling through the pipeline. The nozzle is thus continually closed during the entire sampling procedure so that the operator is not exposed to the material in the pipeline, and the interior of the pipeline is exposed to minimal external contamination.

It is, therefore, an object of this invention to provide a device for taking material samples from a pipeline through which the material being sampled falls vertically.

It is an additional object of this invention to provide a sampling device of the character described wherein the pipeline remains closed to ambient surroundings during the entire sampling procedure.

It is a further object of this invention to provide a sampling device of the character described which is easy to operate and protects the operator from contact with the material being sampled.

These and other objects and advantages of the invention will become more readily apparent from the following detailed description of a preferred embodiment thereof when taken in conjunction with the accompanying drawings, in which:

FIG. 4 is a fragmented sectional view of a pipeline showing the sampling device mounted thereon and in the inward sample-gathering position; and FIG. 5 is a view similar to FIG. 4 but showing the device in its outward sample-releasing position.

Figure 1:
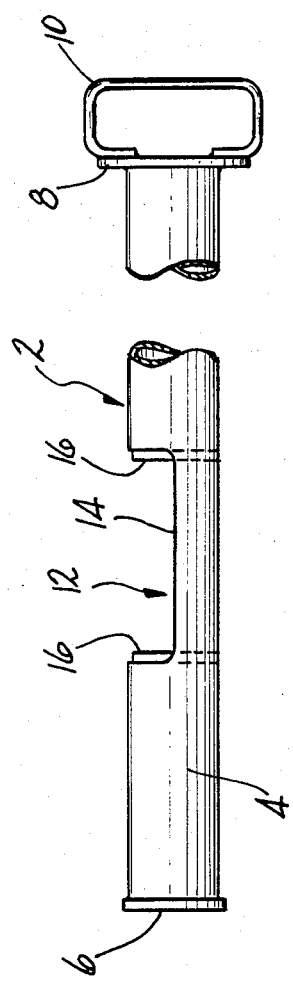
FIG. 1 is a fragmented side elevational view of the scoop part of the sampling device of this invention.
Figure 3:
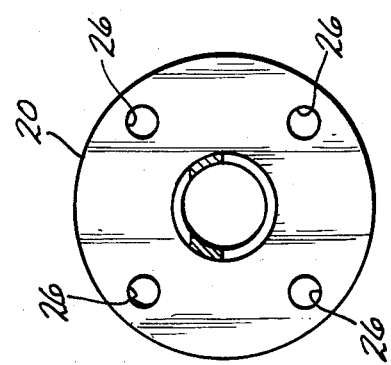
FIG. 3 is a sectional view taken along line 3—3 of FIG. 2.
Figure 2:
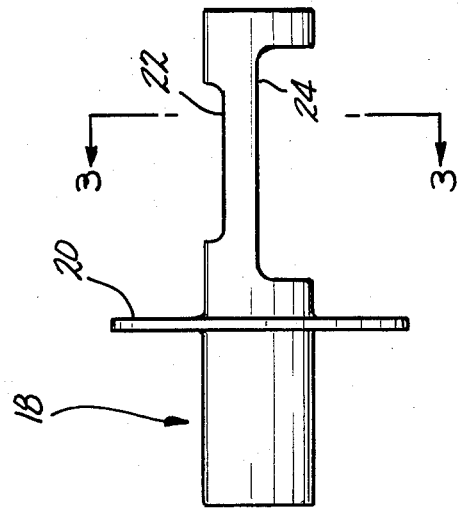
FIG. 2 is a side elevational view of the track part of the sampling device.

Referring now to the drawings, there is shown in FIG. 1 a scoop part, denoted generally by the numeral 2, adapted for use with the sample-gathering device of this invention. The scoop 2 includes a body portion 4 made from stainless steel tubing. One end, the inner end, of the body 4 is closed by a disk 6 welded thereto and the other or outer end of the body 4 is closed by a larger diameter plate 8 welded thereto. A ring handle 10 is welded to the plate 8 for manual actuation of the scoop 2. The upper half of the central part of the body 4 is cut away at 12 to form a cradle portion 14 of the scoop 2 with the ends of the cradle portion 14 being closed off by disks 16 welded to the body 4 to seal off the ends of the interior of the body 4 from the cradle 14. Thus, the cradle 14 is the material-transporting part of the scoop 2. The track 18 is shown in FIG. 2 and it is made from a piece of open-ended stainless steel tubing. A radial flange 20 is welded to the track 18 and a top inspection opening 22 is cut into the track 18. Likewise, a bottom discharge opening 24 is cut into the track beneath the inspection opening 22. The flange 20 is provided with a plurality of bolt holes 26.

Referring to FIG. 4, the device is shown installed on a pipeline 28 through which material drops by gravity in the direction of the arrow A. The pipeline 28 includes a nozzle 30 welded thereto as per the prior art. The track 18 is telescoped into the nozzle 30 and is secured thereto by means of a plurality of bolts 32 which extend through the flange bolt holes 26 and through a back up ring 34. The track flange 20 and the back up ring 34 straddle a flange 36 formed on the nozzle 30. The scoop 2 is telescoped into the track 18 and is shown fully extended thereinto so that the plate 8 abuts the outer end of the track 18. The scoop 2 is rotationally positioned in the track 18 so that the cradle 14 opens upwardly whereby some of the material falling through the pipeline 28 will be deposited in the cradle 14. It is noted that the bore of the nozzle 30 is closed to the ambient surroundings by the track 18 and scoop 2 thereby closing off the pipeline 28 to the ambient surroundings while the sample is being taken. Also, the openings 22 and 24 in the track 18 are closed by the scoop 2 when the sample is taken.

FIG. 5 shows the position of the scoop 2 when the obtained sample is dumped into a receptacle (not shown) for analysis. To remove the sample, the scoop 2 is pulled outwardly of the track 18 until the cradle 14 aligns with the inspection opening 22, whereupon the sample can be seen while still in the scoop 2. If the sample appears acceptable, the scoop 2 is rotated about its axis 180° to the position shown in FIG. 5 so that the sample will drop out of the cradle 14 through the discharge opening 24, as indicated by the arrow B, and into a testing receptacle (not shown). It will be noted that the nozzle 30 remains closed to ambient surroundings during retrieval and discharge of the sample because of the track 18 and scoop 2. Thus, the pipeline 28 is likewise closed. The position of the scoop 2 in the track 18 at discharge, shown in FIG. 5, prevents any of the descending material from passing into the nozzle 30 from the pipeline 28.

It will be readily appreciated that the sampling device of this invention will safely obtain samples from pipelines without exposing the operator to the interior of the pipeline, and without exposing the interior of the pipeline to ambient surroundings. The nozzle fitting will not collect unwanted material from the pipeline during periods between samplings. The sampler can be operated easily by one person without danger of spilling the sample accidentally. The sampler cannot accidentally jam in an open position wherein the interior of the pipeline would be in communication with the ambient surroundings.

Since many changes and variations of the disclosed embodiment of the invention may be made without departing from the inventive concept, it is not intended to limit the invention otherwise than as required by the appended claims.

What is claimed is:

1. A manually operated material sampling apparatus for taking samples of a material from a pipeline equipped with a sample retrieval nozzle opening into said pipeline through the pipeline wall, and wherein the material falls downwardly through the pipeline, said sampling apparatus comprising:
   (a) a radially outwardly extending flange formed at an outer end of said nozzle distal of said pipeline;
   (b) a tubular open-ended track member telescopically engaging said nozzle, said track member having a radially outwardly extending flange thereon which is disposed in abutting contact with said nozzle flange, and said track member having an outward portion which extends from said track member flange away from said pipeline, said track member outward portion having formed therein a vertically upwardly open inspection opening, and an opposed aligned vertically downwardly open discharge opening;
   (c) means removably clamping said track member flange to said nozzle flange; and
   (d) a tubular scoop member telescopically mounted in said track member for axial and rotational reciprocal movement with respect to said track member, said scoop member having a first sealed end disposed in said track member, a second end opposite said first sealed end, said second end being disposed outside of said track member and having a stop part operable to engage said track member to limit the extent to which said scoop member can be telescoped into said track member, and said scoop member further including an open cradle portion disposed between said first and second ends of said scoop member, said scoop member being movable with respect to said track member between;
      (i) an inner sample-catching position wherein said cradle portion is disposed within said pipeline to catch a sample of the material falling through said pipeline and wherein said stop part engages said track member, said scoop member being operable to close off said inspection and discharge openings in said track member when in said sample-catching position; and
      (ii) an outer sample-delivering position wherein said inner sealed end of said scoop member is disposed in sealing relationship with said nozzle and track member to seal the interior of the pipeline from ambient surroundings, and wherein said cradle portion of said scoop member is aligned with said inspection opening in said track member so that a retrieved sample can be visually inspected and dumped from said cradle portion through said discharge opening by appropriate axial rotation of said scoop member.

2. The apparatus of claim 1, further comprising disk means for sealing opposite ends of said cradle portion of said scoop member from opposite interior ends of said scoop member.

* * * * *